United States Patent [19]

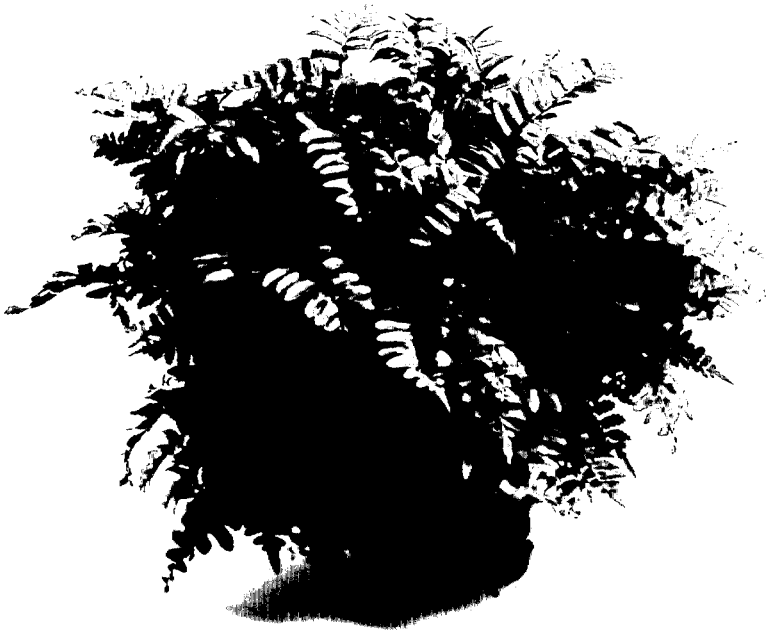

Mills et al.

[11] Patent Number: Plant 5,755

[45] Date of Patent: Jun. 24, 1986

[54] *NEPHROLEPIS EXALTATA* NAMED DALLAS JEWEL

[75] Inventors: Wayne J. Mills; Katherine L. Hampton, both of Herndon, Va.

[73] Assignee: Casa Flora, Inc., Dallas, Tex.

[21] Appl. No.: 694,822

[22] Filed: Jan. 25, 1985

[51] Int. Cl.[4] ..... A01H 9/00

[52] U.S. Cl. ..... Plt./88

[58] Field of Search ..... Plt./88

[56] References Cited

U.S. PATENT DOCUMENTS

P.P. 5,128 10/1983 Hofland ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A new variety and distinct variety of *Nephrolepis exaltata* named Dallas Jewel having the characteristics of closely spaced plantlets, vigorous, full and compact growth habit, non-crown leaf form, loose, feathery and shiny fronds which are unusually short, ease of propagation, less inclination to damage at retail outlets, adaptability to various pot sizes, and its tolerance to lower light levels which make it adaptable to large scale use in interiorscape plantings.

1 Drawing Figure

The present invention comprises a new and distinct cultivar of *Nephrolepis exaltata,* known by the cultivar name Dallas Jewel.

The new cultivar was discovered growing among a group of plants of the parent cultivar in the greenhouses of Dulles Gardens, Inc. in Herndon, Va. in February, 1984. The parent is unnamed, and the plants were obtained from Jones Greenhouse, Panama City, Fla. The new cultivar was immediately recognized for its distinctly different characteristics when compared with the other plants of the parent cultivar, with the compact habit and uniqueness of the fronds being particularly apparent.

After separating the new cultivar from the plants of the parent cultivar, the new cultivar was asexually reproduced at Dulles Gardens, Inc., Herndon, Va., by the present inventors by taking vegetative cuttings from the cultivar. Horticultural examination of subsequent generations of propagation has clearly demonstrated that the combination of characteristics as herein disclosed for Dallas Jewel are firmly fixed and are retained through successive generations of asexual reproduction. Asexual reproduction was followed by selection and reselection and the following description is of a plant obtained through the selection process.

Dallas Jewel has not been observed under all possible environmental conditions. The phenotype may vary significantly with variations in environment such as temperature, light intensity, and day length. The following observations, measurements and comparisons describe plants grown in Herndon, Va. and Dallas, Tex. under greenhouse conditions which approximate those generally used in commercial practice.

The following traits have been repeatedly observed and are determined to be basic characteristics of Dallas Jewel, which in combination distinguish Dallas Jewel as a new and distinct cultivar:

(1) Excellent vigor.

(2) Compact growth habit thereby permitting the plant to be readily grown for production in cell packs.

(3) Perhaps its most distinctive characteristic is its shorter and more closely formed plantlets on the runners, as opposed to known plants of this type which produce long runners from a central crown, and consequently a relatively large plant.

(4) Due to its compactness and shorter fronds, it does not hang over the edge of the pot like other cultivars of this type, and gives a loose feathery unsymmetrical appearance making it appear much fuller than normal.

(5) Due to the abundance of runners and plantlets, the plant can be easily propagated.

(6) Dallas Jewel is a sterile non-spore producing cultivar, thereby requiring reproduction through asexual techniques.

(7) The new cultivar has the unique ability to adapt itself to the size of the pot in which it is planted. Plants produce full and attractive growth without becoming overgrown or pot bound. To the best knowledge of the present inventors, this is a totally unique feature in species of this type.

(8) The attractive bright green color of the fronds can be consistently maintained by a feeding solution including nutrients so as to prevent yellowing of the fronds.

(9) All of the above characteristics together result in an outstanding new cultivar, and market research to date has indicated a probable wide acceptance of the new cultivar.

The accompanying photographic drawing illustrates in perspective view the new cultivar grown in a 6" pot. The color values specified below are prevalent throughout the photograph, although the fronds exposed to light at the top and sides of the plant appear somewhat lighter due to deflected light. The color values were taken in January, 1985, under artificial light conditions.

Attached is Chart A which compares certain characteristics of Dallas Jewel with the same characteristics of the well known fern cultivars named Boston and Boston Compacta. The measurements appearing in the chart were based on observations and measurements of the listed cultivars grown simultaneously in the greenhouses of Casa Flora, Inc., Dallas, Tex. The compactness of Dallas Jewel will be particularly apparent from the comparative measurements.

Dallas Jewel can also be compared with the *Nephrolepis exaltata* cultivar Eleanor, disclosed in U.S. Plant Pat. No. 5,128, granted Oct. 25, 1983. Based on plants of Dallas Jewel and Eleanor grown simultaneously in Dallas, Tex., the respective cultivars can be compared as follows:

(1) The fronds of Eleanor are much longer and wider, measuring 12–14" in length and 2½–3½" in width.

(2) The shape of the fronds are different, with the fronds of Dallas Jewel abruptly tapering from the upper one-fifth of the mature frond to the apex, as compared with more gradual taper of Eleanor from the upper one-third of a mature frond to the apex.

(3) Hairs are absent or sparse on the rachis of Dallas Jewel, and when present they are predominantly at the pinna base. In Eleanor, hairs are more abundant and persistant all along the rachis on mature fronds.

(4) The color of the mature fronds of Dallas Jewel is dark green, as opposed to the light yellowish-green frond color of Eleanor.

(5) The pinnae of Dallas Jewel are prominently toothed, and the apex is obtuse to rounded. In Eleanor, the apex is acute to obtuse.

(6) The individual pinna of Dallas Jewel are much smaller, measuring ¾–1¼" in length and ⅜ up to ½" in width. In Eleanor, each individual pinna is 1½–1¾" long and ½" wide.

(7) The shape of the pinnae are also different, with each pinna in Dallas Jewel being oblong with the sides generally parallel, with tapering appearing only near the apex. By contrast, the pinnae of Eleanor are narrowly ovate, with the sides tapering essentially continuously from the base to the apex.

(8) The number of pinnae is also substantially different, averaging 41 for each mature frond of Dallas Jewel, and 63 for each mature frond of Eleanor.

(9) Dallas Jewel is much more dwarf and compact, with plants averaging 8–12" tall and 18–20" wide. The fronds are erect to spreading, and do not hide the container. By contrast, Eleanor is a much larger and spreading plant, averaging 14–16" tall and 24–30" wide. The fronds are erect to strongly arching and when mature hide the container.

In the following description, color references are made to The Royal Horticultural Society Colour Chart (R.H.S.). The color values were determined at approximately 4:00 p.m. on Jan. 10, 1985 under artificial light conditions in Alexandria, Va.

THE PLANT

Botanical: *Nephrolepis exaltata, Dallas ii,* Ramat., cv Dallas Jewel.

Origin: Mutation of unnamed cultivar.

Form: Compact, informal feathery arrangement of fronds with the luxuriance of a fern; suitable for a table plant, basket, or interiorscape use.

Shape: Compact form but loosely nonsymmetrical; fronds hang loosely but are never long enough to entirely cover the growing container.

Growth: Vigorous, hardy, upright, compact, multirunner with fronds which are sturdy with good strength, cultivar doesn't die out in the center as in other compact cultivars.

Foliage:

*Quantity.*—Abundant; number of leaves makes plant appear fuller than other cultivars of this general type.

*Leaves.*—Shape: Pinnate crenate. Size: Very short; approximately 2" wide and 11" long depending on culture. Margin type: Crenate. Texture: Smooth, soft, fernlike. Gloss: Slight sheen. Pubescence distribution: Only on young fronds and runners but disappearing as leaves become mature. Color: Upper side primarily green 137A; 137B also present; tips somewhat lighter. Under side 137C-D.

*Leaflets.*—Pinna simple with pronounced arching in pinna from midrib; normally opposite. Size: Approximate length of pinna ¾" to 1¼"; approximate width ⅜". Shape: Pinnate crenate. Petiole: Length including rachis approximately 11". Rachis: Length approximately 8¼". Ribs and veins: Pinnate; dark green on mature leaves.

*Buds.*—*Nephrolepis exaltata* cultivar normally produce spores but this mutant is sterile as are many mutants such as *Nephrolepis exaltata bostoneinsis* and its many variants. Asexual or vegetative propagation is therefore necessary.

Other characteristics:

*Nutrient feeding.*—The intense green frond color can be maintained during low light periods by the application of 200 ppm of Peters Soluble Fertilizer (15-16-17). In periods of longer day length, Peters Soluble Fertilizer (20-20-20) can be applied in amounts up to 350 ppm. With such applications, yellowing does not occur, as frequently is the case for ferns of all types.

*Adaptability.*—A remarkable characteristic of Dallas Jewel is its adaptability to different pot sizes and yet maintain its compact, full and controlled growth. Trialling to date has indicated that the same unique and advantageous characteristics noted occur with pot sizes of 4" and 6", for example. This is clearly atypical of most ferns, which tend to grow uncontrollably, usually in the form of excessively long fronds. Dallas Jewel for reasons not presently known is comfortable in pots of various sizes, and maintains its compact and controlled growth regardless of pot size and plant age.

CHART A

| | DALLAS JEWEL | BOSTON | BOSTON COMPACTA |
|---|---|---|---|
| Leaf length, mature: | 11" | 36"+ | 18" |
| Leaf width, mature: | 2½" | 4" | 3" |
| Rachis length: | 8¼" | 30"+ | 13½" |
| Pinna length, mature: | ¾to 1¼" | 2" | 1½" |
| Pinna width, mature: | ⅜" | ⅝" | ½" |
| Pinna petiole length: | 2¾" | 6" | 4½" |

I claim:

1. A new and distinct variety of *Nephrolepis exaltata* named Dallas Jewel, as illustrated and described, and particularly characterized by its closely spaced plantlets, vigorous, full and compact growth habit, non-crown leaf form, loose, feathery and shiny fronds which are unusually short, ease of propagation, less inclination to damage at retail outlets, adaptability to various pot sizes, and its tolerance to lower light levels which make it adaptable to large scale use in interiorscape plantings.

* * * * *